United States Patent [19]

Anner et al.

[11] 4,076,737

[45] Feb. 28, 1978

[54] ALDEHYDES OF THE PREGNANE SERIES AND DERIVATIVES THEREOF

[75] Inventors: Georg Anner, Basel; Charles Meystre, Reinach, both of Switzerland

[73] Assignee: Ciba-Geigy Corporation, Ardsley, N.Y.

[21] Appl. No.: 717,854

[22] Filed: Aug. 26, 1976

Related U.S. Application Data

[63] Continuation of Ser. No. 551,482, Feb. 20, 1975, abandoned, which is a continuation-in-part of Ser. No. 447,791, Mar. 4, 1974, abandoned, which is a continuation-in-part of Ser. No. 883,326, Dec. 8, 1969, abandoned.

[51] Int. Cl.$^2$ .............................................. C07J 17/00
[52] U.S. Cl. ..................... 260/397.45; 260/239.55 C; 260/239.5; 195/51 S
[58] Field of Search .................... 260/239.55 C, 397.45

[56] References Cited

U.S. PATENT DOCUMENTS

| 3,020,275 | 2/1962 | Marx et al. ..................... 260/239.53 |
| 3,501,513 | 3/1970 | Bacso ............................... 260/397.45 |
| 3,519,659 | 7/1970 | Schmidlin et al. ............. 260/397.45 |
| 3,519,660 | 7/1970 | Schmidlin et al. ............. 260/397.45 |

FOREIGN PATENT DOCUMENTS

| 1,257,140 | 12/1967 | Germany ......................... 260/397.45 |

*Primary Examiner*—Elbert L. Roberts
*Attorney, Agent, or Firm*—Theodor O. Groeger

[57] ABSTRACT

The derivatives of 1-dehydro-6α,9α-difluoro-16α-methyl-corticosterone having an aldehyde group in 21-position instead of the hydroxyl group, and derivatives of such aldehydes having a 2-chlorine atom, the corresponding hydrates, as well as their functional aldehyde derivatives, such as the acetals, display an antiinflammatory and thymolytic action. They are prepared by conventional methods.

4 Claims, No Drawings

ALDEHYDES OF THE PREGNANE SERIES AND DERIVATIVES THEREOF

CROSS-REFERENCE TO RELATED APPLICATIONS

The present application is a continuation of application Ser. No. 551,482, filed Feb. 20, 1975, (now abandoned) which is, in turn, a continuation-in-part of application Ser. No. 447,791, filed Mar. 4, 1974 (now abandoned), which is, in turn, a continuation-in-part of application Ser. No. 883,326, filed Dec. 8, 1969 (now abandoned).

SUMMARY OF THE INVENTION

The present invention relates to the manufacture of new 21-aldehydes of the pregnane series and their hydrates, acylates, acetals and hemiacetals, more especially those of the formula

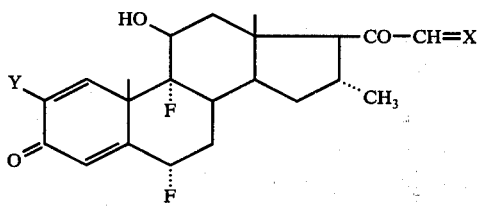

in which formula X denotes the group

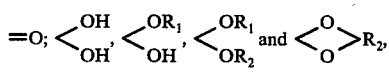

wherein $R_1$ represents an unsubstituted or substituted lower aliphatic or lower araliphatic hydrocarbon residue, $R_2$ represents a lower alkylene group, and wherein Y denotes hydrogen or chlorine.

DESCRIPTION OF THE PREFERRED EMBODIMENTS

In the new compounds of the above formula the said lower aliphatic or araliphatic hydrocarbon residues mentioned can be saturated or unsaturated and are thus for example alkyl groups, especially those having 1–4 C atoms, which can also be substituted, for example hydroxyl groups or halogen atoms, for example chlorine, such as the methyl, ethyl, propyl, isopropyl or butyl group or the -hydroxy-ethyl group, and also alkenyl groups or alkynyl groups preferably having 3 or 4 carbon atoms, such as the allyl group. A lower araliphatic hydrocarbon residue is especially a phenyl-lower alkyl residue having 1 to 4 carbon atoms in the alkyl moiety, for example the benzyl residue. A lower alkylene group is preferably one having 1 to 4 carbon atoms, such as an ethylene or propylene group.

The free aldehydes of the present invention can be present in the ketonic form shown above according to formula (I) or in the form of their tautomeric enol form of formula

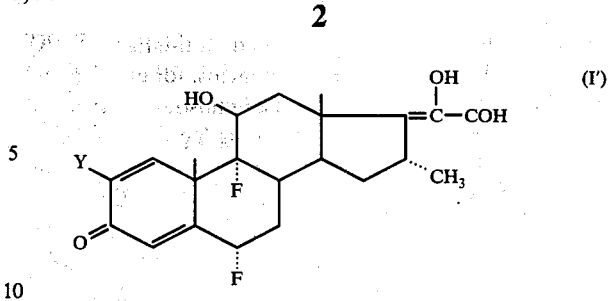

depending on the conditions under which they are prepared and/or isolated. They also react in one or the other tautomeric form depending on the reactants used; thus, for instance, whereas the etherification leads to the aldehyde acetals, the acylation of the free aldehydes produces the $\Delta^{17,20}$-20-enol-acylates.

What is said or implied below concerning the free aldehydes is meant to apply both to the ketonic and the enol form, unless specific reference to one or the other form is made, and the invention is directed to both tautomeric forms and also to derivatives of the enol forms, especially to the 20-enol esters of the compounds of formula (I') and the derivatives thereof in which the 21-aldehyde group is acetalized, viz. the hemiacetals and diacetals of the 20-enol-acylates of the compounds of formula (I'). In these enol esters the acyl group is preferably one derived from organic carboxylic acids of the aliphatic, alicyclic, aromatic or heterocyclic series, especially those with 1 to 18 carbon atoms, especially from lower aliphatic carboxylic acids having from 1 to 7 carbon atoms, e.g. from formic, acetic, propionic, a butyric acid or valeric acid such as n-valeric acid, or from trimethylacetic or trifluoracetic acid, from a caproic acid such as β-trimethyl-propionic acid or diethylacetic acid or oenanthic, caprylic, pelargonic, capric acid, from an undecylic acid, for example undecylenic acid, from lauric, myristic, palmitic or a stearic acid, for example oleic, cyclopropane-, cyclobutane-, cyclopentane- or cyclohexane-carboxylic acid, cyclopropyl-methanecarboxylic, cyclobutylmethanecarboxylic, cyclopentyl-ethanecarboxylic, cyclohexylethanecarboxylic acid from cyclopentyl-, cyclohexyl- or phenyl-acetic or -propionic acids or benzoic acid, or phenoxyalkanoic acids such as phenoxyacetic acid, dicarboxylic acids such as succinic, phthalic or quinolinic acid, or furan-2-carboxylic, 5-tertiary butyl-furan-2-carboxylic, 5-bromo-furan-2-carboxylic acid, from nicotinic or isonicotinic acid, or from sulphonic acids such as benzenesulphonic acids, or of inorganic acids, for example phosphoric or sulphuric acids.

Among the new products there are especially to be mentioned the $\Delta^{1,4}$-16α-methyl-6α,9α-difluoro-11β-hydroxy-3,20,21-trioxo-pregnadiene, its hydrate, its 21-methyl-hemiacetal and 21,21-dimethylacetal, their 2-chloro derivatives and the derivatives corresponding to these compounds having an 11-oxo group instead of the 11β-hydroxy group. Special mention also deserve the 21,21-diethyl or dibenzyl acetals of the $\Delta^{1,4}$-16α-methyl-6α,9α-difluoro-11β-hydroxy 3,20,21-trioxo-pregnadiene and the acetal derived from ethylene glycol. Among the 20-enols of the 21-aldehydes of the present invention according to formula (I') above and their 20-esters there is especially to be mentioned the $\Delta^{1,4,17(20)}$-16α-methyl-6α,9α-difluoro-11β-hydroxy-20-acetoxy-3,21-dioxo-pregnatriene.

The new compounds of the present invention possess valuable pharmacological properties. Thus they especially exhibit a very pronounced anti-inflammatory action as is found in animal experiments, for example on rats, both on local and systemic administration in doses of 0,001 – 30 mg/kg and 0.03 – 3 mg/kg respectively.

Thus, for instance, the 21,21-dimethyl-acetal of the $\Delta^{1,4}$-16α-methyl-6α,9α-difluoro-11β-hydroxy-3,20,21-trioxopregnadiene shows a pronounced anti-inflammatory action in the granuloma test on the rat in a dose interval of 0.3 – 1.0 mg/kg when given subcutaneously and of 0.03 – 0.1 mg/kg when administered orally. When applied topically this compound shows in the granuloma test on the rat a pronounced anti-inflammatory action in a dose range of 0.003 – 0.01 mg/kg. The compound has a thymolytic action on the rat in doses of 0.03 – 0.1 mg/kg when given both subcutaneously and orally.

The new compounds are therefore suitable for use as anti-inflammatory agents. They furthermore show a strong thymolytic action, especially after systemic administration, and they also have an anti-leucaemic activity, as can be shown in animal tests, for instance on rats. They are however also intermediates for the manufacture of other useful substances, especially of pharmacologically active compounds.

The new compounds of the present invention can be manufactured in a manner which is in itself known. More especially they can be obtained when (a) in a compound of the formula

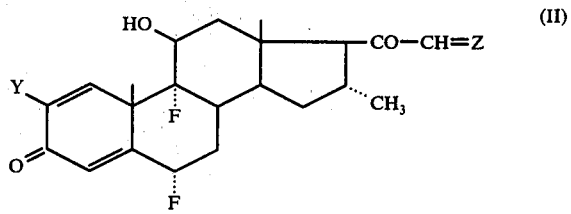

in which Y has the meaning given above for formula (I), and Z represents a residue convertible into the oxo group or into one of the groups

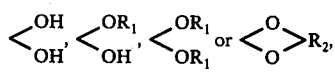

$R_1$ and $R_2$ having the same meaning as given for formula 1, the residue Z is so converted, or when (b) a double bond is introduced into the 1,2-position of a compound of the formula

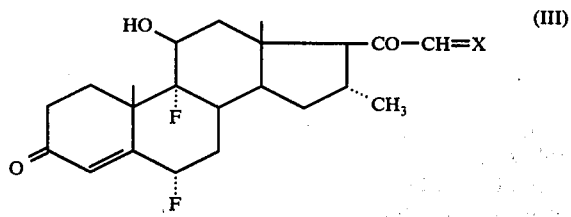

in which formula X has the meaning given for formula (I), or when (c) in a compound of the formula

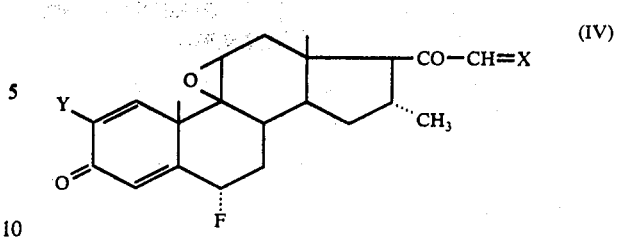

in which formula X and Y have the same meaning as given in formula (I), the 9,11β-epoxide group is split with hydrogen fluoride or with a hydrogen fluoride donor, or when (d) a compound of the formula

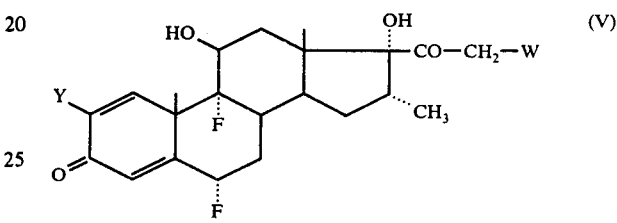

in which formula Y has the same meaning as given in formula (I) and W represents a free hydroxyl group or a secondary amino group, is treated with an acidic medium in an alcoholic solution, or when (e) a compound of the formula

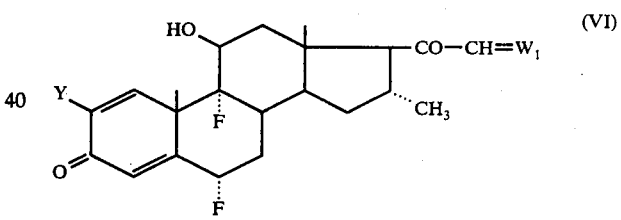

in which formula $W_1$ is an oxo group or one of the groups

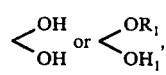

wherein $R_1$ and Y have the same meaning as given in formula (I), is treated with an etherifying and/or esterifying agent or when a compound of the above formula in which $W_1$ represents one of the groups

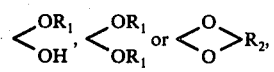

or an 20-enol acylate of such compund or of a compound wherein $W_1$ is oxo is treated with a hydrolysing agent, or when (f) in a compound of the formula

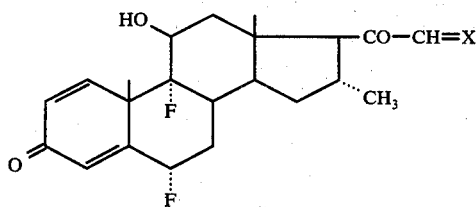

(VII)

wherein X has the meaning given for formula (I) the 1,2 carbon-carbon double bond is selectively saturated, or when (g) in a compound of the formula

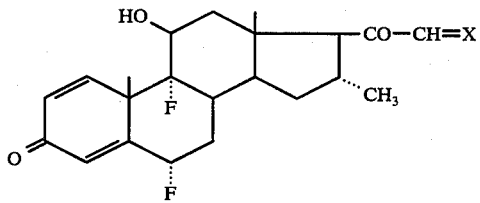

(VIII)

wherein X has the meaning given for formula (I), a chlorine atom is introduced in 2-position.

In formula (II) above a group Z which is convertible into the oxo group or one of the other groups mentioned under (a), that is to say, the hydrates, acylates or acetals of the 21-aldehydes, is especially a free hydroxyl group together with a hydrogen atom. Such group is converted e.g. in known manner into the aldehyde group or one of its derivatives. According to a preferred variant of this process the 21-hydroxy group is converted into a sulphonic acid ester, for example into the para-tosyl ester, the latter is converted with a tertiary aromatic base (for example with pyridine) into the quaternary salt, the salt is converted in a weakly alkaline solution with a para-nitroso-dialkylaniline (for example para-nitroso-dimethylaniline) into the 21-nitrone, and the latter is hydrolyzed with a dilute aqueous mineral acid to the desired 21-aldehyde.

Another generally suitable process is the direct dehydrogenation of the 21-hydroxyl group with reducible metal salts in known manner. The oxidant used is, for example, cupric acetate in a suitable solvent such as methanol or ethanol, if desired or required in the presence of an acid, for example acetic acid. According to a special variant of this dehydrogenation the 21-hydroxypregnane is treated with molecular oxygen in the presence of the above mentioned reducible metal salts, for example cupric acetate, used in a catalytic proportion. Alternatively, the dehydrogenation of the 21-hydroxyl group in the starting materials mentioned may be carried out with selenium dioxide, advantageously in a suitable solvent, such as methanol or glacial acetic acid. The reaction may be accelerated or completed by heating. Finally, the dehydrogenation may also be achieved with manganese dioxide.

In the above formula (II) Z can also represent two halogen atoms, for example two bromine atoms. Such 21,21-dihalogeno compounds can be converted, for example with metal acylates of the first group of the Periodic Table, such as an alkali metal acetate or silver acetate, into the corresponding 21,21-diacylates of the 21,21-dihydroxy compounds, that is to say of the hydrated form of the aldehydes of formula (I), or with an alkali metal alcoholate, for example sodium methylate, into the 21,21-diethers, that is to say, the acetals of the aldehydes of formula (I). The diacylates and diacetals may be converted by alkaline or acid hydrolysis into the free aldehydes or into the corresponding 21,21-dihydroxy compounds.

According to method (b) above a double bond is introduced in compounds of formula (III) with the use of known chemical or microbiological dehydrogenating methods. From among the former there may be mentioned as an example the dehydrogenation by means of selenium dioxide or selenious acid, preferably in a tertiary aliphatic alcohol, such as tertiary butanol or tertiary amyl alcohol or with 2,3-dichloro-5,6-dicyano-1,4-benzoquinone in boiling benzene or dioxan. For dehydrogenation in the 1,2-position a bromine atom may be introduced in known manner in the 2-position which is then eliminated in the form of hydrogen bromide.

The microbiological dehydrogenation is performed, for example, with cultures of microorganisms of the species Corynebacterium simplex, Septomyxa affinis or Didymella lycopersici or with their enzymes isolated from the mycelium.

According to method (c) the $9\beta$, $11\beta$-epoxide group is split in known manner with hydrogen fluoride, using it in the anhydrous form, if desired or required in an inert solvent such as chloroform, tetrahydrofuran or especially dimethylformamide or as aqueous hydrofluoric acid. It is also possible to use a hydrogen fluoride donor, for example a salt of this acid with a tertiary organic base, for example pyridine, or a derivative of hydrofluoric acid. a particularly valuable process has been described and claimed in U.S. specification No. 3,211,758, according to which hydrogen fluoride is used in the form of an adduct thereof with carbamic or thiocarbamic acid, especially with urea.

When method (d) above is used with starting materials having a 21-hydroxyl group, the treatment with an acidic agent may be carried out in an alcoholic or an aqueous medium. As acid agents there may be used for instance an inorganic acid preferably an oxygen free acid, or a Lewis acid. For example, the starting compound is boiled for several hours with an aqueous or alcoholic solution of hydrogen chloride of about 1-2% strength. In aqueous mediums a mixture of the aldehydes or their hydrates in the ketonic form corresponding to formula (I) and of the corresponding enolic form of formula (I') are obtained, whereas in alcoholic solution, especially in anhydrous alcoholic solution, acetals of the ketonic form, and under anhydrous conditions especially the diacetals, corresponding to the alcohol used, are formed.

As alcohols, lower aliphatic alkanols having 1-4 C atoms are especially used, such as methanol, ethanol, propanol, isopropanol the butanols or unsaturated alkanols having preferably 3-4 C atoms such as allyl alcohol or dihydric alcohols such as ethylene glycol or propylene glycol, and also halogenohydrins such as ethylene chlorhydrin. Amongst the lower araliphatic alcohols which can be used in accordance with the process, lower phenylalkanols, for example benzyl alcohol, should be especially highlighted.

If starting materials of the above formula (V) are used, wherein W represents a secondary amino group, the acid treatment is preferably performed in aqueous solution, for instance with hydrochloric acid, or p-toluene sulfonic acid, at a pH of about 2, and the enolic form of the aldehydes corresponding to formula (I') are predominantly obtained in this manner. There may also be added organic solvents such as alcohols or tetrahydrofuran, and the reaction may be carried out at temperatures between 10° and 100°. The secondary amino group in the starting compound is preferably one in which there are two lower aliphatic hydrocarbon radicals attached to the nitrogen atom, such as methyl or ethyl radicals, or one containing an alkylene group or an alkylene group interrupted by further nitrogen atoms, such as a piperidino or piperazino radical.

According to method (e) above free aldehydes or their hydrates or their hemiacetals are treated with etherifying or with esterifying agents, especially with such derived from the above mentioned acids and alcohols, to obtain diacetals, hemiacetals or 20-enol acylates of the aldehydes or of the acetals. Diacetals are obtained in a manner known per se, e.g. by boiling the aldehydes or their hydrates or the 20-enol acylates with an alcohol, preferably in the presence of an acid catalyst such as an inorganic acid or a Lewis acid. Alternatively, the acetals may be formed by reacting the free aldehydes or their hemiacetals or the corresponding hydrates with orthoformic acid esters of the relevant alacohols.

In order to prepare 20-enol acylates of the aldehydes or of the acetals, the free aldehydes, their hydrates or the acetals are treated with acylating agents in a manner known per se, such as carboxylic acid halides or anhydrides, for example those derived from the above mentioned acids, e.g. acetic anhydride, preferably in the presence of a tertiary base, such as pyridine.

According to another feature of the method (e) above the free aldehydes or their hydrates of formula (I) or (I') may be obtained from the just described acetals and acylates by acid or/and alkaline hydrolysis. The acid hydrolysis of acetals can be performed in a manner known per se, for instance by using dilute mineral acids, especially lower aliphatic acids, or perchloric acid. If alkaline agents are selected to carry about hydrolysis of enol-acylates, they should be used under very mild conditions, for instance with dilute alkali metal carbonates or bicarbonates solutions, as under more drastic basic conditions, especially in the pesence of alcohols, the new aldehydes according to the invention will undergo a rearrangement leading to products of different structure.

Hemiacetals can also easily be prepared from the free aldehydes or their hydrates or the 20-enol form of the aldehydes by simply reacting these compounds with an anhydrous alcohol, for instance when crystallizing them in an anhydrous alcohol. From hydroxyl free solvents in the presence of water the hydrates (the 21,21-dihydroxy compounds of formula (I) are formed which, generally, when just left to themselves over phosphorus pentoxide, lose water and pass into the free aldehydes.

Following method (f) above compounds of formula (VII) are selectively hydrogenated in 1,2-position. This reaction may also be performed in a manner known per se. Thus, for instance, the starting compounds are hydrogenated in a homogeneous phase using tris-triphenyl-phosphin - rhodium chloride catalyst.

In order to introduce a chlorine atom in 2-position of compounds of formula (VIII) following procedure (g), the starting compounds are reacted with chlorine, and hydrogen chloride is then split off from the 1,2-dichloro-derivatives obtained. The addition of chlorine is effected for instance by treating the starting compounds in an inert solvent, preferably e.g. dioxan, with a solution of chlorine in a lower aliphatic carboxylic acid, such as propionic acid, at low temperature and in the absence of light. Hydrochloric acid can be split off from the 1,2-dichloro compounds obtained intermediately by reacting the latter with a base, especially with an organic tertiary nitrogen base, such as triethylamine, pyridine or collidine. Prior to the addition of chlorine, any 11-hydroxy group present may advantageously be temporarily esterified, e.g. with a trihalocarboxylic, e.g. trifluoroacetic acid, and the ester group can be split after the treatment with the nitrogen base to form the free 11-hydroxy group.

The starting compounds to be used in the above mentioned processes are known or they can be manufactured in a manner known per se or by methods disclosed in the present application.

The invention also relates to those embodiments of the process in which one starts from a compound obtainable as an intermediate at any stage and carries out the missing process stages or in which a starting material is formed under the reaction conditions.

The present invention also relates to the manufacture of pharmaceutical preparations for use in human or veterinary medicine, which contain the new pharmacologically active substances of the present application, described above, as active substances together with a phramaceutical excipient. Organic or inorganic substances which are suitable for enteral, for example oral, parenteral or topical administration are used as excipients. Possible substances for forming the latter are those which do not react with the new compounds such as for example water, gelatines, lactose, starch, magnesium stearate, talc, vegetable oils, benzyl alcohols, gum, polyalkylene glycols, white petroleum jelly, cholesterol and other known medicinal excipients. The pharmaceutical preparations may be in a solid form, for example as tablets, dragees or capsules, or in a liquid or semi-liquid form as solutions, suspensions, emulsion, ointments or creams. These pharmaceutical preparations are optionally sterilised and/or contain auxiliary substances such as preservatives, stabilisers, wetting agents or emulsifiers, salts for regulating the osmotic pressure or buffers. They can also contain yet further therapeutically valuable substances. The new substances can also serve as starting products for the manufacture of other valuable compounds.

The compounds of the present application can also be used as fodder additives.

The invention is described in more detail in the following examples:

EXAMPLE 1

50 ml of a 1 % strength solution of hydrogen chloride in methanol are poured over 3 g of flumethasone. The reaction mixture is boiled for 3 hours under reflux whilst passing nitrogen through it and whilst stirring, whereupon a clear solution is produced. The solution is then concentrated in vacuo. The dry residue is taken up in methylene chloride and the solution is filtered through 30 g of aluminium oxide (activity II). The methylene chloride eluates on evaporation leaves the crude $\Delta^{1,4}$-16α-methyl-6α,9α-difluoro-11β-hydroxy-21,21-dimethoxy-3,20-dioxo-pregnadiene. On recrystallising the crude product from a methylene chloride-isopropyl ether mixture the pure compound of melting point 186°–188° C is obtained.

EXAMPLE 2

40 ml of a 1 % strength solution of hydrogen chloride in n-butanol are poured over 2 g of flumethansone. The reaction mixture is stirred for 3 hours at 70° C, whereupon a clear solution is produced. This solution is evaporated in vacuo. The residue is dissolved in ethyl acetate and the ethyl acetate solution is washed with dilute potassium bicarbonate solution and water, dried and evaporated in vacuo. The residue is crystallised from a methylene chloride-isopropyl ether mixture and the $\Delta^{1,4}$-16α-methyl-6α,9α-difluoro-11β-hydroxy-21,21-di-n-butoxy-3,20-dioxo-pregnadiene of melting point 154°–155° C is obtained.

EXAMPLE 3

20 ml of a 1 % strength solution of hydrogen chloride in benzyl alcohol are poured over 2 g of flumethasone. The reaction mixture is stirred for 3 hours at 70° C, whereupon a clear solution is produced. The solution is diluted with ethyl acetate and the ethyl acetate solution is washed with dilute potassium bicarbonate solution and water, dried and concentrated in vacuo. The residue is subjected to a vacuumsteam distillation, whereby the excess benzyl alcohol is driven off. The residue, dried in vacuo, is then recrystallised from a methylene chloride-isopropyl ether mixture and the $\Delta^{1,4}$-16α-methyl-6α,9α,difluoro-11β-hydroxy-21,21-dibenzyloxy-3,20-dioxo-pregnadiene of melting point 162°–164° C is obtained.

EXAMPLE 4

50 ml of dioxan and 5 ml of a 1 % strength hydrogen chloride solution in ethylene glycol are poured over 5 g of flumethasone. The reaction mixture is stirred for 4 hours at a bath temperature of 80° C, whereupon a clear solution is quickly produced. The solution is then concentrated in vacuo and the residue is taken up in methylene chloride. Thereafter the solution is chromatographed on 100 g of silica gel and elution carried out with a 2 % solution of t-butanol in methylene chloride, whereupon the crude $\Delta^{1,4}$-16α-methyl-6α,9α-difluoro-11β-hydroxy-21,21-ethylenedioxy-3,20-dioxo-pregnadiene is obtained as a residue from the evaporated eluates. The product is recrystallised from acetone-isopropyl ether mixture, whereupon the pure acetal of melting point 217°–226° C is obtained.

On further elution with solutions of t-butanol in methylene chloride with increasing percentage content of t-butanol further amorphous constituents are obtained which contain $\Delta^{1,4}$-16α-methyl-6α,9α-difluoro-11β-hydroxy-21,21-bis-ω-hydroxy-ethoxy-3,20-dioxo-pregnadiene. In contrast to the monoacetal, they show a strongly associated hydroxyl band in the IR-spectrum.

EXAMPLE 5

Pharmaceutical preparation in the form of an ointment for local use, containing $\Delta^{1,4}$-16α-methyl-6α,9α-difluoro-11β-hydroxy-21,21-dimethoxy-3,20-dioxo-pregnadiene as the active principle:

| composition: | |
|---|---|
| White petroleum jelly } Paraffin oil | 65.0 % |
| Higher fatty alcohols } Waxes | 10.0 % |
| Polyoxyethylene-sorbitane derivatives } | 4.45 % |

| -continued | |
|---|---|
| composition: | |
| Sorbitane-fatty acid esters | |
| Preservatives | 0.2 % |
| Perfume | 0.1 % |
| Water | 20.0 % |
| $\Delta^{1,4}$-16α-methyl-6α,9α-difluoro-11β-hydroxy 21,21-dimethoxy-3,20-dioxo-pregnadiene | 0.25 % |
| perfume | 0.1 % |
| Water | 20.0 % |
| $\Delta^{1,4}$-16α-methyl-6α,9α-difluoro-11β-hydroxy 21,21-dimethoxy-3,20-dioxo-pregnadiene | 0.25 % |

Preparation

The fats and the emulsifiers are fused together, the preservative is dissolved in water and this aqueous solution is emulsified with the melt at an elevated temperature. Whilst the emulsion thus obtained is cooling, a suspension of the active principle in a part of the melt is incorporated into the emulsion and the perfume is then added.

EXAMPLE 6

0,5 g $\Delta^{1,4}$-6α-9α-difluoro-16α-methyl-11β-hydroxy-21,21-dimethoxy-3,20-dioxopregnadiene are dissolved in 25 ml tetrahydrofuran and 75 ml of a 2,6-molar solution of aqueous perchloric acid are added. The solution is subjected for 10 hours to a slow distillation under reduced pressure, while continuously replacing the tetrahydrofuran - water mixture. There are then added 125 ml of water, the main part of the tetrahydrofuran is eliminated by evaporation under reduced pressure. In this way the hydrate of the $\Delta^{1,4}$-6α,9α-difluoro-16α-methyl-11β-hydroxy-3,20,31-trioxo-pregnadiene precipitates.

0,3 g of the aldehyde hydrate obtained is dissolved in 30 ml of methanol and the solution is concentrated to a volume of 12.5 ml after having added 0.03 ml of glacial acetic acid and 120 ml of water. There is thus obtained the 21-methylhemiacetal of $\Delta^{1,4}$-6α,9α-difluoro-16α-methyl-11β-hydroxy-3,20,21-trioxo-pregnadiene.

EXAMPLE 7

1 g of Flumethasone is mixed with 50 ml of tetrahydrofuran and with a solution of 1 ml of concentrated hydrochloric acid in 9 ml of water. The resulting solution is refluxed for 4 hours under nitrogen, then cooled, and mixed with 40 ml of water. The tetrahydrofuran is expelled under reduced pressure, and the resulting suspension is extracted with methylene chloride. Insoluble starting material is filtered off and then washed with methylene chloride. The filtrate is extracted with methylene chloride, the methylene chloride solution are washed with water, dried and evaporated in vacuo. The residue is recrystallized from a small quantity of ether. Crystals of $\Delta^{1,4,17(20)}$-6α,9α-difluoro-16α-methyl-11β,20-dihydroxy-3,21-dioxo-pregnatriene are obtained which melt at 205°–218° C.

In the IR spectrum in methylene chloride, the substance shows, inter alia, hydroxyl bands at 2.88 μ and 3.00 μ; and a broad band between 6.00 μ and 6.25 μ.

In the UV spectrum in rectified alcohol, it shows one maximum at 240 mμ (E = 13720) and another at 286 mμ (E = 10584).

The crude substance undergoes no change when it is purified on alumina (activity II) in tetrahydrofuran, in a rapidly performed chromatography operation.

When the chromatography is performed with other solvents, such as methylene chloride or ethyl acetate either alone or with the addition of alcohol, there is obtained as conversion product of the enol described a mixture containing $\Delta^{1,4}$-6α,9α-difluoro-16α-methyl-11β,hydroxy-3,20,21-trioxo-pregnadiene and its 21-hydrate.

In the IR spectrum, this mixture shows, inter alia, a strong, wide band at 5.95 μ and a narrow band at 6.24 μ. In the U.V. spectrum the band at 286 mμ has disappeared.

EXAMPLE 8

1 g of $\Delta^{1,4}$-6α,9α-difluoro-16α-methyl-11β,17α,21-trihydroxy-2-chloro-3,20-dioxo-pregnadiene (2-chloro-flumethasone) is treated with 40 ml of a freshly prepared 1% methanolic hydrogen chloride solution, and the mixture is refluxed for 4 hours, a clear solution forming soon. The solution is then evaporated under reduced pressure, the residue is dissolved in methylene chloride, and the solution filtered through 10 g of alumina (activity II). The methylene chloride eluates are combined and evaporated, and the residue recrystallized from methylene chloride+isopropylether. $\Delta^{1,4}$-6α,9α-difluoro-16α-methyl-11β-hydroxy-2-chloro-21,21-dimethoxy-3,20-dioxo-pregnadiene is so obtained, which melts at 257° - 260° C. In the IR spectrum (methylene chloride) it exhibits characteristic bands inter alia at 9.40 μ and 9.95 μ. From the mother liquor a small quantity of the same compound can be obtained. It melts at 254° - 256° C.

On hydrolysis of the above acetal according to Example 6 $\Delta^{1,4}$-6α,9α-difluoro-16α-methyl-11β-hydroxy-2-chloro-3,20,21-trioxo-pregnadiene or its $\Delta^{17,20}$-20 enol is obtained.

EXAMPLE 9

100 mg of $\Delta^{1,4}$-6α,9α-difluoro-11β-hydroxy-16α-methyl-21,21-dimethoxy-3,20-dioxo-pregnadiene are mixed with 10 ml of tetrahydrofuran and 30 ml of a 2.66-molar aqueous perchloric acid solution. In an atmosphere of nitrogen the tetrahydrofuran is distilled off slowly and replaced currently by adding dropwise fresh tetrahydrofuran to the boiling reaction mixture. After 5 hours, the cooled solution is agitated with a 3:1 mixture of ether and methylene chloride, the extract is washed with water, dried and evaporated under reduced pressure. Unlike the starting material, the resulting residue rapidly and thoroughly reduces an alkaline silver diamine solution. In the thin-layer chromatogram (silica gel plates, eluting agent: methylene chloride + methanol (95:1); rendering visible with UV light of 254 mμ or with sulfuric acid after short heating to 120° C) two substances are detected, namely: (a) $\Delta^{1,4}$-6α,9α-difluoro-11β-hydroxy-16α-methyl-3,20,21-trioxo-pregnadiene having an Rf value of about 0.4, and (b) $\Delta^{1,4(17)20}$-6α,9α-difluoro-11β,20-dihydroxy-16α-methyl-3,21-dioxo-pregnatriene having an Rf value of about 0.5, the Rf values agreeing with those of the samples of authentic material.

The isolation of the reaction products (a) and (b) can be carried out by chromatography on silica gel, as in Example 10.

EXAMPLE 10

A solution of 2 g of flumethasone ($\Delta^{1,4}$-6α,9α-difluoro-16α-methyl-11β,17α,21-trihydroxy-3,20-dioxo-pregnadiene) in 100 ml of tetrahydrofuran is treated with a solution of 5 ml of concentrated hydrochloric acid in 20 ml of water, and the mixture is refluxed for 10 hours in an atmosphere of nitrogen. After cooling, the solution is treated with 100 ml of water, and the tetrahydrofuran is evaporated under reduced pressure. The resulting suspension is extracted with a 3:1 mixture of ether and methylene chloride, the extract is washed with water, dilute potassium bicarbonate solution, and again with water, dried and evaporated in vacuo. The resulting residue is chromatographed on 60 g of silica gel. The first eluates (methylene chloride with 1% of acetone) yield oily products. There follow eluates whose residues crystallize well from ether. The colorless substance, which melts at 216° - 248° C, is $\Delta^{1,4}$ 17(20)-6α,9α-difluoro-16α-methyl-11β,20-dihydroxy-3,21-dioxo-pregnatriene. On further elution with methylene chloride containing 2-6% of acetone, there are obtained after evaporation of the eluates yellow products which crystallize when dissolved in methylene chloride and precipitated with isopropyl ether. The resulting yellowish substance is the hemihydrate of $\Delta^{1,4}$-6α,9α-difluoro-11β-hydroxy-16α-methyl-3,20,21-trioxo-pregnadiene of the empirical formula $C_{44}H_{54}O_9F_4$. It melts at 130° C.

When the aforementioned yellow eluate residues are treated with water, white crystals of the hydrate of $\Delta^{1,4}$-6α,9α-difluoro-11β-hydroxy-16α-methyl-3,20,21-trioxo-pregnadiene of the empirical formula $C_{22}H_{28}O_5F_2$ are obtained. They can be recrystallized for example from water. In cold water, their solubility is about 0.07% and in warm water about 0.3%. The recrystallized product forms white needles which are insoluble in neutral methylene chloride and can be readily washed therewith. (In acid methylene chloride, on the other hand, they are easily soluble and yield a yellow solution). The product so recrystallized and washed first melts at 147° C then solidifies in microcrystalline form, and melts again at 250° C with decomposition.

Finally, from the further eluates (with methylene chloride and quantities of acetone increasing from 16 to 32%) small quantities of unchanged flumethasone are obtained.

EXAMPLE 11

400 ml of 1-normal hydrochloric acid are added under stirring to 3g of the $\Delta^{1,4}$-21-(piperazinyl-1)-2-chloro-6α,9α-difluoro-16α-methyl-11β,17-dihydroxy 3,20-dioxo-pregnadiene and the mixture is stirred under an atmosphere of nitrogen on a bath of 90° C for 20 hours, during which time the solid suspended partially dissolves and then a crystallization takes place. After cooling the solid is removed by filtration, washed with water and dried. The so obtained crystalline material represents the $\Delta^{1,4,17(20)}$-2-chloro-6α,9α-difluoro-16α-methyl-11β,20-dihydroxy-3,21-dioxo-pregnatriene which melts at 250°-260° with decomposition. The crude product is dissolved in little methylene chloride, the solution thus obtained is diluted with isopropyl ether and the methylene chloride is evaporated off. There is thus obtained the pure product named above melting at 261°-271° C with decomposition. The UV spectrum (in ethanol) shows a maximum at 245 nm (E = 16 700) and another peak at nm 282 (E = 14 140).

The starting material can be preparerd as follows:

5g of 2-chloro-flumethasone are dissolved in 20 ml of pyridine and the solution is cooled down to −18° C. While maintaining this solution at this temperature, a solution of 5 ml of methane sulfonic acid chloride, cooled also to −18° C, in 20 ml of pyridine, is added, and the mixture is left to stand for one hour in an ice-water bath. It is then poured on ice, the mixture is extracted with ethyl acetate and the organic layer is washed successively with dilute hydrochloric acid, water, dilute potassium bicarbonate solution and again with water. After drying the solvent is evaporated off in vacuo. The 21-mesylate of the 2-chloroflumethasone thus obtained is dissolved in tetrahydrofuran, and N-methyl-piperazine is added under nitrogen. The solution is heated for 20 hours at 55° C, then diluted with ethyl acetate, the ethyl acetate layer washed with water, then dried and freed from the solvent by evaporation under vacuum at 55°. The residue thus obtained forms the $\Delta^{1,4}$-(21-piperazinyl-1)-2-chloro-6α,9α-difluoro-16α-methyl-11β,17α-dihydroxy-3,20-dioxo-pregnadiene.

The 20-acetate of the $\Delta^{1,4,17(20)}$-2-chloro-6α,9α-difluoro-16α-methyl-11β,20-dihydroxy-3,21-dioxo-pregnatriene can be obtained as follows:

1g of the free 20-hydroxy compound last named is dissolved in a mixture of 5 ml of pyridine and 5 ml of acetic acid anhydride. The solution is kept at 20° C for 15 hours; ice is then added, the suspension is extracted with ethyl acetate, the organic layer washed successively with dilute hydrochloric acid, water, dilute potassium bicarbonate solution and again with water, then dried and freed from the solvent in vacuo. The residue represents the desired 20-acetate named above.

EXAMPLE 12

100 ml of tetrahydrofuran and a solution of 5 ml conc. hydrochloric acid in 20 ml of water are added to 2.5g of 2-chloro-flumethasone. The solution is kept boiling, in an atmosphere of nitrogen, and while stirring, for 8 hours. The tetrahydrofuran is then removed by evaporation in vacuo and the residue is extracted with ether. The ethereal solution is washed with water, dried and evaporated in vacuo. The residue is chromatographed on 70g of silica gel. From the residues of the first eluates, obtained with methylene chloride, there is obtained by crystallization from iso-propyl ether the $\Delta^{1,4,17(20)}$-2-chloro-6α,9α-difluoro-16α-methyl-11β,20-dihydroxy-3,21-dioxo-pregnatriene melting at 261°-271° C (with decomposition). No depression results in melting in admixture with the same compound as obtained in Example 11. Both compounds also have identical UV absorption spectra in alcohol, a maximum at 245 nm (E = 16 700) and another peak at 282 nm (E = 14 140). The subsequent eluates obtained with methylene chloride and those obtained with a 2% - solution of acetone in methylene chloride are evaporated together, the residue is dissolved in little methylene chloride, and cyclohexane is added. Then the whole batch is concentrated by evaporation and the $\Delta^{1,4}$-2-chloro-6α,9α-difluoro-16α-methyl-11β,hydroxy-3,20,21-trioxo-pregnadiene of melting point 130° separates out. In its UV-spectrum, (in ethanol) it shows a maximum at 245 nm (E = 15 600).

We claim:

1. A 20-acylate of the $\Delta^{1,4,17(20)}$-16α-methyl-6α,9α-difluoro-11β,20-dihydroxy-3,21-dioxo-pregnatriene, in which the acylate group is derived from a lower aliphatic carboxylic acid having from 1 to 7 carbon atoms.

2. A compound as claimed in claim 1, which is the 20-acetate of the $\Delta^{1,4,17(20)}$-16α-methyl-6α,9α-difluoro-11β, 20-dihydroxy-3,21-dioxo-pregnatriene.

3. A 20-acylate of the $\Delta^{1,4,17(20)}$-2-chloro-6α,9α-difluoro-16α-methyl- 11β,20-dihydroxy-3,21-dioxo-pregnatriene, in which the acylate group is derived from a lower aliphatic carboxylic acid having from 1 to 7 carbon atoms.

4. A compound as claimed in claim 3, which is the 20-acetate of the $\Delta^{1,4,17(20)}$-2-chloro-6α,9α-difluoro-16α-methyl-11β,20-dihydroxy-3,21-dioxo-pregnatriene.

* * * * *